(12) United States Patent
Fichtali et al.

(10) Patent No.: US 7,678,931 B2
(45) Date of Patent: Mar. 16, 2010

(54) PROCESS FOR PREPARING MATERIALS FOR EXTRACTION

(75) Inventors: Jaouad Fichtali, Lexington, KY (US); Anand Sundararajan, Louisville, KY (US)

(73) Assignee: Martek Biosciences Corporation, Columbia, MD (US)

(*) Notice: Subject to any disclaimer, the term of this patent is extended or adjusted under 35 U.S.C. 154(b) by 707 days.

(21) Appl. No.: 11/255,787

(22) Filed: Oct. 21, 2005

(65) Prior Publication Data
US 2006/0122410 A1 Jun. 8, 2006

Related U.S. Application Data

(60) Provisional application No. 60/621,158, filed on Oct. 22, 2004.

(51) Int. Cl.
*C11B 1/00* (2006.01)
(52) U.S. Cl. ......................................... 554/20
(58) Field of Classification Search ........................ None
See application file for complete search history.

(56) References Cited

U.S. PATENT DOCUMENTS

| | | | |
|---|---|---|---|
| 4,296,099 A | | 10/1981 | Berrebi et al. |
| 4,349,540 A | | 9/1982 | D'Hinterland et al. |
| 4,455,298 A | | 6/1984 | McFarlane et al. |
| 4,776,173 A | | 10/1988 | Kamarei et al. |
| 4,857,329 A | | 8/1989 | Sako et al. |
| 5,130,242 A | | 7/1992 | Barclay |
| 5,162,506 A | * | 11/1992 | Hadden ................ 530/412 |
| 5,340,594 A | | 8/1994 | Barclay |
| 5,397,591 A | | 3/1995 | Kyle et al. |
| 5,407,957 A | | 4/1995 | Kyle et al. |
| 5,492,938 A | | 2/1996 | Kyle et al. |
| 5,539,133 A | | 7/1996 | Kohn et al. |
| 5,658,767 A | | 8/1997 | Kyle |
| 5,711,983 A | | 1/1998 | Kyle et al. |
| 6,255,505 B1 | | 7/2001 | Bijl et al. |
| 6,441,208 B2 | | 8/2002 | Bijl et al. |
| 6,566,123 B1 | | 5/2003 | Barclay |
| 6,727,373 B2 | | 4/2004 | Bijl et al. |
| 2003/0143659 A1 | | 7/2003 | Bijl et al. |

FOREIGN PATENT DOCUMENTS

| WO | WO 87/03951 | 7/1987 |
|---|---|---|
| WO | WO 03/092628 | 11/2003 |

OTHER PUBLICATIONS

"Particulate Processing" printed Dec. 1, 2003, available at http://www.niroinc.com/html/drying/fluidbed.html.
Traub, "Fluid Bed Dryers" printed Dec. 1, 2003, available at http://process-heating.com/CDA/ArticleInformation/Drying.Files_Item/0,3274,23976, . . . .
Srinivasakannan et al., Chem. Biochem. Eng. Q. 17(3) 201-205 (2003).
Written Opinion for International (PCT) Patent Application No. PCT/US05/38252; mailed Oct. 23, 2006.
International Preliminary Report On Patentability for International (PCT) Patent Application No. PCT/US05/38252; issued Apr. 24, 2007.
International Search Report for international application; No. PCT/US05/38252; Oct. 23, 2006.

\* cited by examiner

*Primary Examiner*—Sandra Saucier
*Assistant Examiner*—Satyendra K Singh
(74) *Attorney, Agent, or Firm*—Sheridan Ross P.C.

(57) ABSTRACT

The present invention relates to a process for preparing a biomass, such as from a microbial fermentation, for an extraction process to separate desired chemicals, nutritional products, bioactive components, proteins, carbohydrates, and lipids, from the biomass. Particularly preferred substances to extract include docosahexaenoic acid, docosapentaenoic acid, and arachidonic acid. The present invention also includes extracting the prepared biomass. Biomasses to be treated in accordance with the methods of the invention include plant, animal, and microbial biomass, particularly a microorganism such as *Crypthecodinium cohnii* and a fungus such as *Mortierella alpina*.

41 Claims, No Drawings

PROCESS FOR PREPARING MATERIALS FOR EXTRACTION

REFERENCE TO RELATED APPLICATION

The present application claims priority under 35 U.S.C. §119(e) of U.S. provisional patent application No. 60/621,158 filed Oct. 22, 2004 which is incorporated herein by reference in its entirety.

FIELD OF THE INVENTION

The present invention relates to a process for preparing a biomass, such as from a microbial fermentation, for an extraction process to separate chemicals, nutritional products, proteins, and fatty acids from the biomass.

BACKGROUND OF THE INVENTION

The beneficial effects of increased dietary intake of long-chain omega-3 fatty acids in humans has been well documented, and includes the reduction of cardiovascular and inflammatory disease (i.e. arthritis and atherosclerosis), reduction of depression, increasing length of gestation in the third trimester, and inhibiting tumor growth. These lipids may be obtained from, for example, a number of heterotrophic marine organisms.

Besides beneficial fatty acids and lipids, many other desired substances, such as, for example, chemicals, nutritional products, proteins, antioxidants, carbohydrates, and other bioactive components, may be obtained from plant, animal, and/or microbial materials or biomass. A general scheme for obtaining these substances includes obtaining a biomass, preparing the biomass for extraction, and subjecting the biomass to extraction, i.e., separating the desired substance from the remainder of the biomass.

A number of different processes have been utilized to prepare a biomass for extraction. Generally, such processes have been 'wet', i.e., carried out with the addition of solvent. For example, for a fermentor-grown microbial biomass, a solid/liquid separation may be carried out to separate the cells from the fermentation broth, and a solvent added back prior to a homogenization step. Generally, a homogenization step requires addition of solvent to allow for efficient homogenization, a disadvantage in that the solvent must be removed before further processing of the biomass. The homogenization step may be carried out by a number of different processes, such as by the use of bead mills, grinding, and so on. See, for example, U.S. Pat. Nos. 4,296,099, 4,349,540, 4,429,969, and 4,455,298, all of which disclose grinding processes to prepare extracts from biological materials. These references, among others, have taught homogenization at various temperatures, such as, for example, room temperatures, elevated temperatures, freezing temperatures, and brittleness temperatures. For example, Kamarei, U.S. Pat. No. 4,776,173, teaches cryogrinding at brittleness temperatures in order to minimize particle size and avoid the use of solvent during the comminution of biomass step.

Generally, for recovery of oil from microbial biomass, extraction is begun from a biomass which has been subjected to drying and/or washing, without an accompanying cell breakage step. See, for example, Barclay, U.S. Pat. No. 5,340,594 and Bijl, U.S. Pat. No. 6,441,208. These publications generally teach a pretreatment step of a wet biomass cake including a drying step to remove water, to reduce problems such as emulsions forming upon organic solvent extraction, and to reduce the amount of solvent needed. Other publications describe crushing a dried biomass in a ball mill. However, none of these publications teach the present invention's novel methods for preparing a biomass for extraction. Surprisingly, the methods of the present invention provide many benefits that would not be expected, including an unexpected increase of yields of desired products during subsequent extraction processes.

In extraction processes, the physical form of the feed, e.g., the particle size and density, can affect the efficiency of the process. This efficiency can be determined in terms of using less solvent or energy, faster processing rate, higher percent recovery, and higher quality of the final products. Generally, it is important that the particle size be small, in order to expose as much as possible of the molecular species to the solvent. However, small particle sizes can cause difficulties in solid-liquid separation, clogging or a high pressure drops across certain types of extractors such as for example, percolation extractors. However, larger particle sizes, due to reduced contact between solvent and desired substance, tend to decrease yields.

Accordingly, although there exist in the art a number of processes to prepare a biomass for extraction, there remains a need in the art to maximize the yields and effectiveness of extraction steps, to improve the economy of these time consuming and expensive processing steps. Such preparation methods can be improved to result in subsequent extraction steps having greater yields; improve quality of the extracted products; and increase ease of extraction.

SUMMARY OF THE INVENTION

The inventors have found that, surprisingly, a novel process for preparing a biomass which includes the steps of freezing a biomass at or below its brittleness temperature, comminuting the frozen biomass, and agglomerating the biomass to produce an agglomerated biomass, confers a number of surprising advantages to the products of a later extraction of the biomass and to the method of extraction, such as, for example, improved efficiency of extraction, and improved qualities of the final product.

In one aspect, the process of the present invention provides for a pasteurization step performed on the biomass, preferably before the freezing step. In another aspect, the present invention provides for drying the biomass before the freezing step, preferably to a moisture level of no more than about 5 to 15% by weight. Drying steps useful in the present invention include spray drying, fluidized bed drying, lyophilization, freeze drying, tray drying, vacuum tray drying, drum drying, and vacuum mixer/reactor drying, for example. An antioxidant can optionally be added to the biomass, preferably before the freezing step, and antioxidants may include, for example, ascorbyl palmitate, tocopherols, citric acid, ascorbic acid, TBHQ, rosemary extract, and lecithin and any mixtures also referred to as antioxidant cocktails. In another aspect, an enzyme may be added to the biomass, preferably during the agglomeration process. Suitable enzymes include proteases (such as ALCALASE™), cellulases, carbohydrases (such as glucoamylase, alpha amylase), and lipases.

A suitable biomass to subject to the process of the present invention includes a biological material, including animal materials, plant materials, and/or microbial materials. Suitable microorganisms include a microorganism such as an algae, bacteria, fungi and/or protist. Preferred organisms are marine microorganisms including order Dinophyceae (dinoflagellates), Stramenopiles (golden algae), and order Thraustochytriales. Preferred microorganisms are of the genus *Thraustochytrium* (including *Ulkenia*), genus Schizochytrium, genus Althornia, genus Aplanochytrium, genus Japonochytrium, genus Labyrinthula, genus Labyrithuloides, species Crypthecodinium cohnii, genus Mortierella, and mixtures thereof. More preferred microorganisms include Crypthecodinium cohnii and the fungus Mortierella alpina.

To accomplish the freezing step, suitable methods include air freezing, blast freezing, fluidized bed freezing, plate freezing, liquid immersion freezing, cryogenic freezing, liquid nitrogen freezing, dry ice freezing, and $CCl_2F_2$ freezing. Preferred methods include contacting the biomass with liquid nitrogen. Suitable methods by which comminuting may be accomplished include crushing, using such crushing devices such as jaw crushers, gyrator crushers, smooth roll crushers, and toothed roll crushers; grinders, using such grinding devices such as hammer mills and impactors, roller mills, pin mills, and ball mills; and homogenization devices such as blenders. A preferred comminution device is a pin mill.

In another aspect, the present invention provides a method for extracting a substance from a biomass, comprising preparing a biomass for extraction, comprising freezing the biomass at or below its brittleness temperature, comminuting the frozen biomass at a temperature no higher than the brittleness temperature, and agglomerating the biomass to produce an agglomerated biomass; and extracting the substance from the agglomerated biomass. In a preferred embodiment, the substance to be extracted is a lipid. Preferred lipids include acyglycerols, phosphoglycerides, fatty acids, sphingolipids, gangliosides, phospholipids, waxes, tocopherols, tocotrienols, sterols, carotenoids, pigments, polyphenols, and antioxidants. Preferably, the lipid is a PUFA having a carbon chain length of at least 20 or at least 22, and preferably has at least three or at least four double bonds. In a preferred embodiment, the lipid is docosahexaenoic acid (at least 10, 20, 30, 40, 50 or 55 weight percent), docosapentaenoic acid (at least 5, 10, 15, or 20 weight percent), arachidonic acid (at least 10, 20, 30, 40 or 50 weight percent) and/or eicosapentaenoic acid (at least 10, 20, 30, 40 or 50 weight percent). In other embodiments, the substance comprises a protein, a saccharide, an isoflavone, a flavonoid, a phytochemical, an antioxidant, a lutein, a lycopene, a saponin, or any other compound with nutraceutical or pharmaceutical benefit, or a nucleotide.

A suitable method for agglomerating the biomass comprises extrusion of the comminuted biomass to form an agglomerated biomass. A preferred temperature in which to extrude the biomass includes a temperature between about 0° C. and about 120° C., with preferred temperature ranges from about 10° C. and about 60° C. and from about 20° C. and about 30° C.

In a preferred embodiment, the biomass is mixed with a dry agent prior to the agglomerating step. Surprisingly, the inventors have found that adding a dry agent to the biomass prior to the agglomerating step increases the eventual yield of substance from the biomass. Dry agents that are compatible with the present invention include many different types of dry agents, such as, for example, plant starches, plant fibers, biomeals, and oilseed hulls. Preferred agents include rice flour and peanut hulls. The dry agent may be added to the biomass at a final concentration of between about 1 weight percent and about 50 weight percent (dry weight). Preferred amounts to add are between about 5 weight percent and about 30 weight percent. Preferably, the porosity is such that about 50% of the volume of the particle comprises air.

The optional extraction step to extract the desired substance from the biomass can be any extraction step known in the art. Preferred methods include solvent extraction, either aqueous or organic. Preferred solvents for extraction include hexane and isohexane. Other preferred methods include near critical extraction, such as, for example, propane extraction, supercritical extraction, such as, for example, $CO_2$ extraction; enzyme-assisted extraction, microwave extraction and mechanical pressing. Preferred types of extraction devices for the present invention include percolation extractors, immersion type extractors, spray and packed extraction towers, an agitated packed tower extractor, such as, for example, a Scheibel column; a mixer/settler extractor, a perforated-plate extraction tower, and a baffle tower. Particularly preferred is percolation extraction.

In other aspects, the present invention also includes a composition prepared by the methods of the present invention. Typically, where the substance to be extracted is a lipid, methods of the present invention result in a percent recovery of lipid (based on weight of lipid in the biomass) of at least about 70%, at least about 80%, at least about 90%, and typically between about 80% and about 95%.

In a most preferred embodiment, the present invention includes a method for extracting a lipid from a microbial biomass, which includes the following steps. The process includes freezing the microbial biomass at or below its brittleness temperature; comminuting the biomass at a temperature no higher than its brittleness temperature to produce a comminuted biomass; adding a dry agent to the comminuted biomass, extruding or pelletizing the biomass to produce an extruded or pelletized biomass; and percolation extracting the lipid from the extruded biomass.

Another embodiment of the invention is biomass useful for extraction produced by a process that includes freezing the biomass at or below its brittleness temperature. The frozen biomass is comminuted at a temperature no higher than the brittleness temperature to produce a comminuted biomass, and the comminuted biomass is agglomerated to produce an agglomerated biomass. In this embodiment, the comminuted biomass can have a particle size of between about 5 μm to about 50 μm and the moisture content of the comminuted biomass can be between about 5% by weight and about 50% by weight. The biomass can further include a dry agent. The step of agglomerating can be conducted by extrusion, and can produce an agglomerated biomass having a particle size from about 0.1 mm to 12 mm, from about 0.3 mm to 10 mm, or from about 2 mm to 3 mm. The bulk density of the agglomerated biomass can be between about 400 $kg/m^3$ to about 1100 $kg/m^3$, between about 400 $kg/m^3$ to about 900 $kg/m^3$, or between about 400 $kg/m^3$ to about 600 $kg/m^3$. The porosity of pellets in the agglomerated biomass can be between about 40% and about 60%, between about 45% and about 55%, and can be about 50%.

A further embodiment of invention is a biomass useful for extraction produced by a process that includes freezing a biomass comprising a marine microorganism selected from the group consisting of order Dinophyceae (Dinoflagellates), Stramenopiles (golden algae), and order Thraustochytriales at or below its brittleness temperature. The frozen biomass is comminuted at a temperature no higher than the brittleness temperature to produce a comminuted biomass that is agglomerated to produce an agglomerated biomass. In this embodiment, the microorganism can be a microorganism selected from the group consisting the genus Thraustochytrium, genus Schizochytrium, genus Althornia, genus Aplanochytrium, genus Japonochytrium, genus Labyrinthula, genus Labyrithuloides, genus Crypthecodinium, and genus Mortierella or it can be a microorganism is selected from the group consisting of Crypthecodinium cohnii and the fungus Mortierella alpina. The comminuted biomass can have a particle size of between about 5 mm to about 50 mm, and can have a moisture content between about 5% by weight and about 50% by weight. The biomass can further include a dry agent. In this embodiment, the step of agglomerating can be conducted by extrusion, and the agglomerated biomass can have a particle size from about 0.1 mm to 12 mm or a bulk density between about 400 kg/m$^3$ to about 1100 kg/m$^3$. The porosity of pellets in the agglomerated biomass can between about 40% and about 60%.

DETAILED DESCRIPTION

The present invention provides for an improvement in efficiency and ease of extraction of substances from a biomass. In accordance with one embodiment of the present invention, a method for preparing a biomass for extraction is provided. The inventors have discovered improved methods by which a biomass may be prepared for extraction. More specifically, the inventors have discovered that the efficiency of extraction can be improved by new methods of preparing a biomass for extraction, comprising freezing the biomass to or below its brittleness temperature to produce a frozen biomass, comminuting the biomass at a temperature at or below its brittleness temperature to produce a comminuted biomass, and agglomerating the comminuted biomass to produce an agglomerated biomass. Preferably, the biomass is then extracted using methods known in the art to isolate a desired substance from the biomass.

One embodiment of the present invention includes a method for preparing a biomass for extraction, which comprises freezing a biomass at or below its brittleness temperature, comminuting the frozen biomass to produce a comminuted biomass, and agglomerating the comminuted biomass to produce an agglomerated biomass. Typically, a biomass suitable for treatment by the processes of the present invention is a biological material selected from an animal material, a plant material, or a microorganism. If the biomass is a plant material or animal material, all customary sanitary practices should be performed when handling the plant or animal material. For example, a biomass should be chilled promptly to low temperature (at or near 0 C). This treatment prevents or drastically reduces undesirable microbial growth, enzymatic activity, and autolytic chemical reactions. Just before freezing, larger tissues should be cut into relatively small pieces (i.e., typically, one to five grams). This procedure will improve the freezing rate and facilitate handling during the comminution step. Attempts should be made to minimize pretreatment time. Microorganisms compatible with the present invention are cultured in a suitable medium in accordance with methods known in the art.

Suitable microorganisms include a microorganism such as an algae, bacteria, fungi and/or protists. Preferred organisms are marine microorganisms including microorganisms of the order Dinophyceae (dinoflagellates), Stramenopiles (golden algae), and order Thraustochytriales. Preferred microorganisms are of the genus *Thraustochytrium*, genus *Schizochytrium*, genus *Althornia*, genus *Aplanochytrium*, genus *Japonochytrium*, genus *Labyrinthula*, genus *Labyrithuloides*, genus *Crypthecodinium* and mixtures thereof. More preferred microorganisms include *Crypthecodinium cohnii*, *Schizochytrium* sp., and the fungus *Mortierella alpina*. It should be noted that many experts agree that *Ulkenia* is not a separate genus from the genus *Thraustochytrium*. Accordingly, as used herein, the genus *Thraustochytrium* will include *Ulkenia*.

Suitable organisms may be obtained from a number of publicly available sources, including by collection from the natural environment. For example, the American Type Culture Collection currently lists forty-five available strains of *Crypthecodinium cohnii*, identified as ATCC Nos. 30021, 30334-30348, 30541-30543, 30555-30557, 30571, 30572, 30772-30775, 30812, 40750, 50050-50060, and 50297-50300. As used herein, any microorganism, or any specific type of organism, includes wild strains, mutants, or recombinant types. Growth conditions in which to culture these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, and U.S. Pat. No. 5,711,983, all of which are incorporated herein by reference in their entirety.

A biomass obtained from a microorganism can refer to a biomass that has not been separated from the culture media in which the biomass organism was cultured. An example of a culture media is a fermentation broth. Preferably, however, the biomass is separated from its culture media by a solid/liquid separation prior to treatment by methods of the present invention. Typical solid/liquid separation techniques include centrifugation, filtration, and membrane filter pressing (plate and frame filter press with squeezing membranes). This (harvested) biomass usually has a dry matter content varying between 5% and 60%. If the water content is too high, the biomass may be dewatered by any method known in the art, such as, for example, centrifugation, filtration, membrane filter press drying, spray drying, fluidized bed drying, lyophilization, freeze drying, tray drying, vacuum tray drying, drum drying, and vacuum mixer/reactor drying. In preferred embodiments, before the comminution step of the invention, the biomass may have up to about 50% moisture by weight. Preferably, the moisture content is less than about 25%, less than about 15%, less than about 10%, and less than about 5%.

In one embodiment, the biomass may be pasteurized either prior to or during the methods of the present invention. Preferably, pasteurization is employed after the fermentation reaction is complete, but before a solid/liquid separation step for removing the biomass from the fermentation broth. The benefits of pasteurization include preventing exposure of the production organism to the environment and inactivating unwanted enzymatic activities. Depending on the species of the production organism, pasteurization is performed at temperatures of from 60° C. to 100° C. The pasteurization may be accomplished by heating directly with steam into the fermentor or indirectly, through heat exchangers. The following preferred pasteurization conditions may be employed, especially for organisms of the genus *Mortierella* and *Crypthecodinium*. The fermentation broth is suitably pasteurized at from about 50° C. to about 95° C., preferably from about 60° C. to about 90° C., and more preferably from about 65° C. to about 85° C. In a batch pasteurization process, pasteurization may take place for between 30 and 90 minutes, preferably from 50 to 75 minutes, and optimally, from 55 to 65 minutes, and can be performed by any suitable heating means known in the art. Preferably, the broth may be cooled or allowed to cool after pasteurization, for example, to about 25° C. or less, (preferably to about 5° C. or less, to about 10° C. or less, to about 15° C. or less, or to about 20° C. or less), before further processing. In a continuous High Temperature Short Time (HTST) process, the pasteurization time can vary from 15 seconds to 5 minutes. Pasteurization temperatures can remain the same. Prior to pasteurization, a deaeration step to remove entrained bubbles and lower the dissolved oxygen concentration may also be necessary. This can be performed by any suitable deaeration means known in the art.

Optionally, an antioxidant may be added to the biomass or the fermentation broth before subjecting the same to the processes of the present invention, or at any point during the processes. Such an antioxidant may help preserve the desired products. For example, polyunsaturated fatty acids may become oxidized at the double bond sites, which may preclude their use in foods and other applications. The oxidative state and stability of a lipid may be measured in a number of ways known in the art, and descriptions of many of these techniques are available from the American Oil Chemist's Society, as well as from other sources. Suitable antioxidants may be chosen by the skilled artisan. Preferred antioxidants include ascorbyl palmitate, tocopherols, citric acid, ascorbic acid, tertiary butyl hydroquinone (TBHQ), rosemary extract, lecithin, and mixtures thereof. Particularly preferred antioxidants include a mixture of (a) ascorbic acid, (b) ascorbyl palmitate and (c) a tocopherol, added at concentrations known in the art. Preferred concentrations for these antioxidants are: 0.2-5% ascorbic acid, 0.1-1% ascorbyl palmitate, and 0.1-1% tocopherol.

Optionally, an enzyme or combination of enzymes may be added to the biomass during any point during the processes of the present invention, including before the freezing step. A typical point at which to add an enzyme is after the comminution step, or during the agglomeration step. Enzymes may be utilized to aid breakdown of cell walls of the biomass to liberate desired products, such as lipids. Suitable enzymes include proteases (such as ALCALASE™), cellulases, carbohydrases (such as glucoamylase and alpha amylase), lipases, and combinations thereof. Suitable concentrations in which to use an enzyme can be determined by one skilled in the art. Surfactants may be added to the enzymes to allow for greater efficiency of later extraction. Processes for the enzyme treatment of biomass for the recovery of lipids are disclosed in U.S. Patent Application No. 60/377,550, entitled "HIGH-QUALITY LIPIDS AND METHODS FOR PRODUCING BY ENZYMATIC LIBERATION FROM BIOMASS," filed on May 3, 2002; PCT Patent Application Serial No. PCT/US03/14177 entitled "HIGH-QUALITY LIPIDS AND METHODS FOR PRODUCING BY ENZYMATIC LIBERATION FROM BIOMASS," filed on May 5, 2003; and copending U.S. patent application Ser. No. 10/513,576, entitled "HIGH-QUALITY LIPIDS AND METHODS FOR PRODUCING BY LIBERATION FROM BIOMASS," filed on Oct. 22, 2004, the disclosures of which are hereby incorporated by reference.

Optionally, the biomass can be heat treated at any points during the processes of the present invention, including before the freezing step. Typical points at which to heat treat the biomass include after the comminution step and during the agglomeration step. In particular embodiments, the step of heat treating includes raising the temperature of the biomass to a temperature of between about 20° C. and about 100° C., between about 30° C. and about 80° C., and between about 40° C. and about 60° C.

The present invention includes the step of freezing the biomass. Particularly for oil-containing biomass, the biomass, at normal milling, grinding, extraction and/or homogenization temperatures, could be viscous and sticky, rendering the materials difficult to work with. The level of stickiness may depend on water content, free oil content and the composition of the biomass. For example, due to their viscous and sticky natures, these materials generally do not flow or pour freely, and tend to adhere to containers and to moving parts of machines. Further, because the materials are in such a viscous and sticky state, breaking the cell walls/cell membranes of the materials is difficult, causing reduced yields of desired products. Therefore, the biomass is frozen to or below a temperature where it turns brittle and fragile such that when subject to a mechanical force or pressure, the biomass fractures, at least in part, rather than flow. The biomass may also be brought to temperatures below the brittleness temperature. The brittleness temperature for a given tissue or material depends on the species and composition of the tissue or material (water, lipids, proteins, carbohydrates, minerals) and thermal properties. Typically, for a biomass of the present invention, and particularly, for a microbial biomass, the desired brittleness is achieved at a temperature between about 0° C. and about −80° C. A preferred temperature at which to freeze the biomass is between about −20° C. and about −60° C., between about −30° C. and about −50° C.

Generally, a fast freezing process is preferred in order to minimize processing time and preserve quality. Many processes for relatively quick freezing are known in the art, and include air freezing, blast freezing, fluidized bed freezing, plate freezing, liquid immersion freezing, cryogenic freezing, liquid nitrogen freezing, dry ice freezing, and $CCl_2F_2$ freezing. Preferred methods include freezing via liquid nitrogen or dry ice. The freezing step may be accomplished by direct contact (e.g., injection) or indirectly.

Upon obtaining the frozen biomass, the frozen biomass may be transferred to any appropriate size reduction equipment to be comminuted. The term 'comminuted' includes any size reduction method known in the art, especially size reduction techniques such as crushing, homogenization, grinding and milling. Suitable comminution devices include those known in the art. Preferred comminution devices include a crushing-type device, such as a jaw crusher, gyrator crusher, smooth-roll crusher, and toothed-roll crusher; a grinding-type device, such as hammer mills, roller mills, pin mills, ball mills; and a homogenization-type device such as a blender. A preferred comminution device is a pin mill. Preferably, the biomass is kept at or below its brittleness temperature throughout the comminution process, until the biomass has achieved the desired particle size. For example, in a preferred process, liquid nitrogen is injected during the comminuting process and during collection of the comminuted biomass to optimize the process and/or quality of the comminuted biomass and/or downstream products.

The step of comminuting is conducted until a desired particle size is achieved. Appropriate particle sizes can be chosen depending on the type of subsequent extraction process to be used. A preferred particle size is from about 5 µm to about 50 µm, a more preferred range is from about 5 µm to about 30 µm, and a most preferred range is from about 5 µm to about 20 µm.

In accordance with the present invention, the process further comprises an agglomeration step. Upon completion of the comminuting process, preferably, the biomass is in the form of a frozen, fine, free-flowing powder, which may contain granular lumps. The inventors have surprisingly found that an additional agglomeration step, preferably incorporating a dry agent into the biomass, has the effect of increasing the overall yield of products, especially a lipid product, when compared to an extraction starting with a frozen, comminuted biomass that has not been agglomerated.

The term 'agglomeration' refers to the process of forming larger particles from smaller ones, and may be accomplished by pelletizing, extruding, granulating, flaking, or otherwise forming larger particles of the comminuted biomass. The frozen comminuted biomass is preferably thawed or allowed to thaw so that it is deformable and can be agglomerated. For example, the comminuted biomass may be brought to a temperature of greater than about 0° C., greater than about 2° C., and less than about 25° C. A preferred temperature is less than about 25° C., and preferably a temperature of about 4° C.

To prepare for an agglomeration step, the biomass may optionally have its moisture content adjusted, so that the moisture level is between about 5% and about 50% by weight, preferably between about 5% and about 20%, and most preferably between about 5% and about 15%. If the moisture content is higher than desired, the biomass can optionally be mechanically dewatered, as described above. If moisture is lower than desired, steam or water could be added during agglomeration.

Preferably, to obtain a suitable moisture level, a dry agent is added to the biomass. The addition of a dry agent confers a number of advantages besides simply lowering moisture level, including, for example, improving the consistency of the biomass, acting as a binder to help retain the integrity of an agglomerated product during any subsequent extraction steps, and improving the porosity of the biomass, which improves solvent percolation during, for example, subsequent extraction steps. The dry agent may be added to the biomass at a final concentration of between about 1 weight percent and about 50 weight percent (dry weight). Preferred amounts to add are between about 5 weight percent and about 30 weight percent. Preferably, the porosity is such that about 50% of the volume of the particle comprises air.

Suitable dry agents include any agent that decreases the overall moisture of the biomass. Preferred agents include plant starches, such as wheat bran, oats and rice flour; plant fibers such as cellulose; biomeals derived from, for example, microorganisms or plant proteins; and oilseed hulls such as peanut, soybean or cottonseed hulls. Preferred dry agents include rice flour and peanut hulls. The dry agent may be added at some point after comminution. Mixing of the dry agent with the comminuted biomass may be accomplished by methods known in the art, for e.g., with tumble blenders, ribbon blenders and double arm mixers. Ribbon blender is the preferred equipment for mixing the dry agent with the biomass.

The biomass, with or without added dry agent, is then agglomerated. A number of agglomeration techniques may be employed. Any appropriate agglomeration technique known in the art that leads to particles with the desired qualities is compatible with the present invention. A preferred type of agglomeration method is extrusion (discussed more fully below). Other types of agglomeration technique include tumbling agglomeration, where a tumbling or rotating drum or cone dryer allowing the particles to adhere to each other. Another type of agglomeration technique compatible with the present invention includes pressure agglomeration, accomplished by a piston, roller, and isostatic processes. Other potential methods to agglomerate the biomass include spherical agglomeration or balling, flaking, spray congealing, cryopelletization, melt spheronization, wet granulation and spray drying with fines recirculation. In order to preserve quality and limit oxidation, agglomeration could be achieved under vacuum using a Littleford Day Reactor for instance or using nitrogen sparging or blanketing.

In a preferred embodiment of the invention, agglomeration is accomplished by an extrusion process. The biomass is preferably agglomerated in such as way as to be suitable for the eventual extraction process. For example, a particle size that is too small may not allow for the use of a percolation extraction process, since the pressure drop over the biomass bed may be too great using particles with an average size below a certain amount. Small particles may also not sink in a solvent and/or may cause clogging of extractors and/or other equipment used downstream of extraction. Too large a size may impede efficient penetration of solvent into the particles during extraction.

For the preferred extrusion process, the biomass should be in an extrudable form. The water content can be adjusted, if necessary, depending on the condition of the biomass, the microorganisms employed, and the extrusion conditions. A dewatering process, as described previously, can remove water, or dry agents added as discussed above. A person skilled in the art can adjust the biomass in this way to the correct consistency. An example of a preferred consistency is that of a paste. A skilled person may adjust the actual extrusion conditions in order to obtain granular biomass particles having the desired structure and size.

The extrusion conditions can be adjusted to minimize product degradation due to excessive mechanical shear or pressures in the extrusion equipment in order to ensure optimal protection of any labile, oxidation-sensitive compounds against oxidation-induced degradation. For instance nitrogen sparging and antioxidants could be used to protect the oil. The extrusion can be conducted at a wide range of temperatures, for example, at a range of from about 0° C. to about 120° C., but is preferably conducted at lower temperatures, in the range of about 10° C. to about 60° C., and more preferably from about 20° C. to about 30° C. During the extrusion, the biomass is usually forced through a barrel towards a die plate, often by a screw. The agglomerated particles may form naturally, the extrudate falling away under its own weight away from the die plate by the influence of gravity, thereby forming particles. However, the agglomerated biomass particles may also be cut to form particles of a desired size. The extrusion barrel is preferably not heated and is more preferably cooled to about 4° C.

As extrusion at normal temperature generally does not change the water content of the biomass, if it is desired to change the water content, methods for dewatering the biomass and/or increasing the solids content of the biomass as disclosed herein may be used. Alternatively, water or steam could be injected during extrusion to improve agglomeration if necessary. For extraction processes or for subsequent storage of the agglomerated particles of biomass, it is desirable for the moisture content to be less than about 25% by weight, from about 5% to about 15% by weight, or to be about 10% by weight moisture. Thus, optionally, the agglomerated biomass may be dried after the agglomeration step, preferably under conditions that allow the agglomerated biomass to remain intact. The drying can be accomplished using techniques as described above. The particles of agglomerated biomass may have a diameter of about 0.1 mm to about 12 mm, more preferably from about 0.3 mm to about 10 mm, more preferably from about 1.5 mm to about 6 mm, and most preferably from about 2 mm to about 3 mm. The length of the particles of agglomerated biomass may be from about 2 to about 5 or about 6 times the diameter. Preferably, the agglomerated particles are fairly uniform in size. The bulk density of the particles will generally be from about 400 kg/m$^3$ to about 1100 kg/m$^3$, more preferably from about 400 kg/m$^3$ to about 900 kg/m$^3$, and more preferably from about 400 kg/m$^3$ to about 600 kg/m$^3$.

Preferably, the agglomerated biomass particles are porous in order to allow an extraction solvent access to the substance to be extracted. Preferably the porosity is such that from about 40% to about 60%, preferably from about 45% to about 55%, and preferably about 50% of the volume of the particle is air, and the porosity will be uniform throughout the particle. The porosity of the particles is dependent on the moisture content and/or composition of the granules. Porosity is defined as the total void volume in an individual pellet divided by the total volume of the pellet based on its exterior dimensions.

A further embodiment of the present invention is a method for extracting a substance from a biomass that has been prepared as described above. Various processes are known in the art for extracting substances from a biomass and these processes are compatible with the methods of the present invention. In particular, a number of processes are known in the art for extracting lipids from a biomass, such as, for example, aqueous extraction; solvent extraction, such as hexane extraction or direct saponification via KOH and ethanol; near critical extraction, such as extraction with propane; supercritical extraction, such as extraction with $CO_2$ or propane; enzyme-assisted extraction; microwave extraction and mechanical pressing. Extraction methods can be modified to extract different types or components of the lipids, as is known by the skilled artisan.

In a preferred embodiment, a desired substance to be extracted comprises a lipid. A preferred lipid includes an acylglycerol, a phosphoglyceride, a fatty acid, a sphingolipid, a ganglioside, a phospholipid, a wax, a tocopherol, a tocotrienol, a sterol, a carotenoid, a pigment, a polyphenol, an antioxidant, and a combination of these compounds. More preferred lipids to extract include triacylglycerols and phosphoglycerides.

A preferred lipid to obtain using methods of the present invention is a polyunsaturated fatty acid (PUFA). A PUFA of the present invention includes a C18, C20, C22, or C24 omega-3 or omega-6 PUFA. Preferably, the PUFA is a C20 or C22 omega-3, or a C20 omega-6 polyunsaturated fatty acid. Preferably, a PUFA of the present invention is a long chain PUFA, which includes C18 and longer PUFAs. A PUFA of the present invention contains at least two double bonds and preferably, three double bonds, and even more preferably at least four double bonds. In particular, the PUFA includes docosahexaenoic acid (at least 10, 20, 30, 40 or 50 weight percent), docosapentaenoic acid (at least 5, 10, 15, or 20 weight percent), arachidonic acid (at least 10, 20, 30, 40 or 50 weight percent) and/or eicosapentaenoic acid (at least 10, 20, 30, 40, or 50 weight percent). In a most preferred embodiment, the lipid to be extracted includes a PUFA having a carbon chain length of at least 20.

In another embodiment, the extraction method is designed to recover a protein. Aqueous or solvent based extraction methods specifically designed for the particular protein may be used. Particularly preferred proteins to extract include functional proteins such as enzymes, peptides, and glycoproteins. In another embodiment, preferred substances to extract include an isoflavone, a flavonoid, a phytochemical, an antioxidant, a lutein, a lycopene, and a saponin.

A preferred lipid extraction is extraction with an effective amount of solvent. Suitable solvents may be determined by those of skill in the art. Polar lipids (e.g. phospholipids) are generally extracted with polar solvents (e.g., a chloroform/methanol system) and neutral lipids (e.g., triacylglycerols) are generally extracted with nonpolar solvents, (e.g., hexane.) Suitable solvents for a triacylglycerol extraction are n-hexane, isohexane, ethyl acetate, isopropyl alcohol, or a mixture of hexane and isopropyl alcohol. Hexane or isohexane are the preferred extracting solvents. A suitable ratio of hexane to prepared biomass is about 4 liters of hexane per kilogram of biomass. The hexane can be mixed with the biomass in a stirred reaction vessel at a temperature of about 20-55° C. for about 1-8 hours. After mixing, the biomass is filtered and separated from the hexane containing the oil. The hexane is removed from the oil by distillation techniques known in the art. Conventional oilseed processing equipment is suitable to perform the filtering, separation, and distillation. Additional processing steps, known to those of skill in the art, can be performed if required or desirable for a particular application. Methods for lipid recovery are described in the following references which are incorporated by reference herein in their entirety: PCT Publication WO 0176715, entitled "A Method for Fractionation of Oil and Polar Lipid-Containing Native Raw Materials"; PCT Publication WO 0176385, entitled "A Method for the Fractionation of Oil and Polar-Lipid Containing Native Raw Materials Using Alcohol and Centrifugation"; PCT Publication WO 0153512, entitled "A Solventless Extraction Process."

Extraction devices known in the art are compatible with the present invention, such as, for example, percolation type extractors, immersion type extractors, spray and packed extraction towers, agitated packed tower extractors, mixer-settler extractors, perforated plate extractor towers, and baffle towers. The preferred device with which to extract the prepared biomass is with a percolation-type extractor. Generally, a column is filled with agglomerated particles prepared by the methods of the present invention, and a solvent (e.g., hexane) is used to cover the agglomerated particles. A solvent temperature of 20-55° C. is used. The solvent may be passed once over the column or preferably it may be recirculated multiple times, e.g., for about three to about seven times, and most preferably about five times. The contact time for the solvent with the column is typically from about half an hour to about one and a half hours, and preferably is for about one hour. The solvent is circulated by means of a pump. Other types of percolation extractors can be employed, such as, for example, cross-current or conveyor-type percolation extractors. Both concurrent and countercurrent extraction methods could be used. Countercurrent extraction such as the use of a Crown Extractor is preferred.

In other aspects, the present invention also includes a composition prepared by the methods of the present invention. Typically, where the substance to be extracted is a lipid, methods of the present invention result in a percent recovery of lipid (based on weight of lipid in the biomass) of at least about 70%, at least about 75%, at least about 80%, at least about 82%, at least about 84%, at least about 86%, at least about 88%, at least about 90%, at least about 92%, and most preferably, at least about 95%.

In a preferred embodiment, the present invention includes a composition that is compatible with and meets the requirements for the organic products market. Such compositions include oil produced as described above, such as by using $CO_2$ supercritical extraction to produce crude oil from a biomass. Such a crude oil can be physically refined, refined with silica treatment or with potassium hydroxide or by another method compatible with organic product market requirements.

The present invention, while disclosed in terms of specific methods, products, and organisms, is intended to include all such methods, products, and organisms obtainable and useful according to the teachings disclosed herein, including all such substitutions, modifications, and optimizations as would be available to those of ordinary skill in the art. The following examples and test results are provided for the purposes of illustration and are not intended to limit the scope of the invention.

EXAMPLE 1

This example describes cryogenic milling of dried *Crypthecodinium cohnii* biomass and subsequent extraction, and compares cryogenic milling to 'wet' milling.

*Crypthecodinium cohnii* was grown in a fermentation medium. The *Crypthecodinium cohnii* biomass was separated from the fermentation broth and spray dried. The biomass was fed into a screw conveyer which had inline liquid nitrogen addition. Biomass thus cryogenically frozen was milled using a Pin mill (Contraplex CW250). The biomass feed rate to the mill was varied. The product conveying airflow rate, which affects the retention time of the product inside the mill, was also changed. Biomass feed rates ranged from 180-500 lb/hr. Airflow rates ranged from 200-400 scfm. A Coulter Counter (LS Particle Size Analyzer) was used to obtain particle size distributions. Analysis showed significant reduction in particle size. For two of the samples used in the experiment, median particle sizes of the unmilled biomass were 43 and 45 µm. The median particle sizes of the samples after being cryogenically milled were 19 and 15 µm, respectively.

The milled material was then subjected to immersion type extraction. Benchtop extraction/washing experiments were done with the milled and unmilled samples. Three solvents were used: n-hexane, ethyl acetate, and hexane/isopropyl alcohol (IPA) in a ratio of 3 to 2 by volume. A test tube containing one gram of the biomass was mixed with 12 mL of the solvent. After sufficient mixing with a vortex mixer, the slurry was spun down on a benchtop centrifuge and the supernatant miscella was discarded. Successive washes were done till there was no visible oil in the miscella (no color change). Four washes were needed. The spent biomass was dried to remove all solvent.

Fatty Acid Methyl Ester (FAME) assay was performed on all starting biomass and spent biomass samples to determine the oil content. FAME estimation may be carried out by following procedures disclosed in Morrison and Smith, A Preparation of Fatty Acid Methyl Esters and Dimethylacetals from Lipids with Boron fluoride-methanol, Journal of Lipid Research, Vol. 5, 1964, and the American Oil Chemist's Society Official Methods.

The amount of oil recovered from the biomass was estimated by two different methods. In one method, the weight of the spent biomass sample was subtracted from that of the starting unextracted sample. The difference (weight of extracted oil) was divided by the weight of oil in the starting unextracted sample (as determined by the FAME assay).

In the second method, the residual oil in the spent biomass was determined by the FAME assay. Subtracting this amount from the total oil weight in the starting sample gave the amount of extracted oil. Dividing the amount of extracted oil by the total oil in the starting sample resulted in % recovery. The Table below summarizes all the results.

TABLE 1

Percent oil recovery of non-agglomerated biomass, measured by either spent biomass (biomeal) weight or biomeal FAME

| Sample | Description | Feed Rate (lb/hr) | Air Flow Rate (scfm) | Oil Content in Feed Sample (%) | % Oil Recovery based on biomeal weight | | | % Oil Recovery based on biomeal FAME | | |
|---|---|---|---|---|---|---|---|---|---|---|
| | | | | | Hexane | Hexane/IPA | Ethyl Acetate | Hexane | Hexane/IPA | Ethyl Acetate |
| 1 | Unmilled | | | 23 | 6.4% | −8.6% | 37.6% | 50.7% | 53.0% | 59.1% |
| 1 | Milled | 500 | 400 | 23 | 49.8% | 59.8% | 63.0% | 80.7% | 84.3% | 82.5% |
| 1 | Milled | 500 | 200 | 23 | 68.1% | 70.3% | 71.0% | 87.7% | 89.6% | 88.5% |
| 1 | Milled | 400 | 200 | 23 | 59.2% | 75.6% | 74.9% | 90.0% | 92.3% | 91.1% |
| 2 | Unmilled | | | 36 | 31.8% | 45.6% | 47.4% | 49.7% | 55.1% | 53.9% |
| 2 | Milled | 230 | 300 | 36 | 60.5% | 69.4% | 76.1% | 70.4% | 72.3% | 71.4% |
| 2 | Milled | 187 | 300 | 34 | 65.8% | 80.1% | 83.7% | 70.5% | 74.3% | 74.1% |
| 3 | Unmilled | | | 35 | 41.1% | 57.5% | 66.5% | 57.5% | 60.4% | 62.2% |
| 3 | Milled | 230 | 300 | 34 | 55.5% | 69.2% | 67.9% | 67.8% | 73.0% | 67.5% |
| 4 | Unmilled | | | 36 | −1.6% | 11.5% | 25.8% | 30.1% | 33.6% | 34.4% |
| 4 | Milled | 200 | 300 | 34 | 17.9% | 47.5% | 48.6% | 55.1% | 59.1% | 56.8% |
| 4 | Milled | 187 | 300 | 34 | 35.2% | 50.6% | 52.2% | 57.9% | 61.1% | 59.6% |

These results demonstrate extraction due to cryomilling of the biomass. As evident, % oil recoveries ranged from 47-92%. Recovery of oil by extraction of cryogenically milled biomass was comparable to the recovery from conventional wet milling technology (mixing dried biomass (unmilled) with solvent (e.g. hexane)), sending the resulting slurry through a homogenizer to break the cells and release the oil, separating the oil laden miscella from the biomeal solids using solid-liquid separators, and evaporating the miscella to recover the crude oil).

EXAMPLE 2

This Example shows the recovery of oil from biomass which was cryogenically milled and extracted with or without dry agent.

*Crypthecodinium cohnii* biomass was obtained as described in Example 1. The biomass was frozen by direct contact with liquid nitrogen, and then milled using a Pin mill as described in Example 1. The cryogenically milled material was allowed to thaw, and was then mixed with one of two types of dry agent (rice flour or peanut hulls) at either 10% by weight, 20% by weight, or 30% by weight; or was not mixed with additional dry agent. The material was then agglomerated by extrusion using Gusta Cold Press (Model 11), which is a single screw extruder/expeller. Different extrusion temperatures were tested: 20° C., 40° C., or 60° C. Table 2 shows the results for an immediate extraction following agglomeration; Table 3 shows the results for a freezing step (i.e., freezing the extruded biomass) followed by extraction. The amount of lipid was determined by either weights or by FAME measurement, both as described in Example 1.

TABLE 2

Percent recovery, measured by either weight or FAMEs, of cryogenically milled *Crypthecodinium cohnii* biomass agglomerated at various temperatures either with or without dry agent, dry agent at 10%, 20%, or 30% by weight. Biomass extracted immediately after agglomeration.

| Experimental Conditions | | | % residual oil in extracted biomass 1st run | % recovery based on weights 1st run | % recovery based on FAMES 1st run |
|---|---|---|---|---|---|
| Agglomeration temp. | % dry matter | Type dry agent | | | |
| 40° C. | 10% | Peanut hulls | 6.7 | 86.8 | 86.2 |
| 20° C. | 20% | Peanut hulls | 4.8 | 87.1 | 88.6 |
| 40° C. | 20% | Peanut hulls | 4.0 | 100.8 | 90.7 |
| 60° C. | 20% | Peanut hulls | 5.1 | 101.7 | 86.4 |
| 40° C. | 30% | Peanut hulls | 1.8 | 110.9 | 93.8 |
| 40° C. | 10% | Rice Flour | 6.4 | 92.9 | 85.6 |
| 20° C. | 20% | Rice Flour | 3.1 | 102.8 | 92.0 |
| 40° C. | 20% | Rice Flour | 6.0 | 90.9 | 85.1 |
| 60° C. | 20% | Rice Flour | 5.1 | 97.6 | 87.1 |
| 40° C. | 30% | Rice Flour | 5.0 | 83.6 | 84.4 |
| 20° C. | | No added dry matter | 7.1 | 97.2 | 87.0 |
| 40° C. | | No added dry matter | 12.4 | 81.3 | 74.6 |
| 60° C. | | No added dry matter | 9.8 | 91.8 | 81.5 |

TABLE 3

Percent recovery, measured by either weight or FAMEs, of cryogenically milled *Crypthecodinium cohnii* biomass agglomerated at various temperatures either with or without dry agent, dry agent at 10%, 20%, or 30% by weight. Biomass extracted immediately after agglomeration.

| Experimental Conditions | | | % residual oil in extracted biomass 2nd run | % recovery based on weights 2nd run | % recovery based on FAMES 2nd run |
|---|---|---|---|---|---|
| Agglomeration temp. | % dry matter | Type dry agent | | | |
| 40° C. | 10% | Peanut hulls | 8.0 | 79.4 | 82.2 |
| 20° C. | 20% | Peanut hulls | 4.1 | 87.4 | 90.4 |
| 40° C. | 20% | Peanut hulls | 3.8 | 94.5 | 90.4 |
| 60° C. | 20% | Peanut hulls | 4.4 | 96.7 | 88.2 |
| 40° C. | 30% | Peanut hulls | 2.3 | 120.0 | 92.4 |
| 40° C. | 10% | Rice Flour | 7.7 | 92.7 | 82.4 |
| 20° C. | 20% | Rice Flour | 3.2 | 106.1 | 92.0 |
| 40° C. | 20% | Rice Flour | 4.4 | 97.7 | 89.5 |
| 60° C. | 20% | Rice Flour | 3.8 | 92.3 | 90.4 |
| 40° C. | 30% | Rice Flour | 1.9 | 98.7 | 94.4 |
| 20° C. | | No added dry matter | — | 70.8 | 64.0 |
| 40° C. | | No added dry matter | 8.4 | 88.6 | 83.6 |
| 60° C. | | No added dry matter | 7.6 | 92.5 | 85.8 |

1. Starting biomass % oil was measured by FAME assay
2. The biomass was extracted and the actual weight of the oil was determined
3. The actual weight of biomeal was also measured
4. The % oil in the extracted biomass (or residual oil in biomeal, as it's also referred) was determined by FAME assay The % recovery based on weight was calculated as follows:
% rec (by wt.)=(Actual weight of oil collected/weight of oil in the biomass as predicted by the FAME assay)*100%

The % recovery based on FAME was calculated as follows:
% rec (by FAME)=((Weight of oil in biomass as predicted by the FAME assay–(% oil in biomeal by FAME*weight of biomeal collected))/(Weight of oil in biomass as predicted by the FAME assay)*100%

The data from Table 2 and Table 3 shows that the observed recoveries of oil were the highest for the biomass that was agglomerated with a dry agent before extraction. The recovery improved as the amount of dry agent was increased from 10% to 20%, and improved again upon increase from 20% to 30%. Heating the biomass during the agglomeration step did not appear to improve recovery. Further improvements could be achieved by techniques known in the art such as pretreatment of extruded biomass with heat, freeze-thaw cycles, enzymatic treatment, adjustment of extraction temperature, solvent to solid ratio, number of extraction stages, and bed depth in percolation methods.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A method for extracting a lipid from a microbial biomass, comprising:
   (a) preparing the microbial biomass by a process, comprising:
      (i) freezing the microbial biomass at or below its brittleness temperature to produce a frozen microbial biomass;
      (ii) comminuting the frozen microbial biomass at a temperature no higher than the brittleness temperature to produce a comminuted biomass;
      (iii) thawing the comminuted biomass to at least a temperature at which the comminuted biomass is deformable;
      (iv) adding an effective amount of a dry agent to the thawed comminuted biomass to achieve an extrudable consistency;
      (v) extruding the comminuted biomass from step (iv) to produce an extruded biomass; and
   (b) percolation extracting the lipid from the extruded biomass.

2. The method of claim 1, wherein at least 70% by weight of the lipids in the biomass are extracted.

3. The method of claim 1, wherein at least 90% by weight of the lipids in the biomass are extracted.

4. The method of claim 1, further comprising pasteurizing the biomass.

5. The method of claim 4, wherein pasteurizing is performed prior to the freezing.

6. The method of claim 1, further comprising separating the biomass, prior to step (a), from a culture medium in which the biomass was cultured.

7. The method of claim 6, wherein the separated biomass is dried.

8. The method of claim 7, wherein the drying is selected from the group consisting of centrifugation, filtration, membrane filter press drying, spray drying, fluidized bed drying, freeze drying, tray drying, vacuum tray drying, drum drying, and vacuum mixer/reactor drying.

9. The method of claim 7, wherein the moisture content of the biomass is less than about 25% by weight.

10. The method of claim 1, wherein an antioxidant is added to the biomass.

11. The method of claim 10, wherein the antioxidant is added to the biomass prior to freezing.

12. The method of claim 10, wherein the antioxidant is selected from the group consisting of ascorbyl palmitate, tocopherols, citric acid, ascorbic acid, tertiary butyl hydroquinone (TBHQ), rosemary extract, lecithin, and mixtures thereof.

13. The method of claim 1, wherein the biomass comprises a microorganism selected from the group consisting of an algae, bacteria, fungi and protist.

14. The method of claim 13, wherein the microorganism is a marine microorganism selected from the group consisting of order Dinophyceae (Dinoflagellates), Stramenopiles (golden algae), and order Thraustochytriales.

15. The method of claim 13, wherein the microorganism is a microorganism selected from the group consisting the genus *Thraustochytrium*, genus *Schizochytrium*, genus *Althornia*, genus *Aplanochytrium*, genus *Japonochytrium*, genus *Labyrinthula*, genus *Labyrithuloides*, genus *Crypthecodinium*, and genus *Mortierella*.

16. The method of claim 13, wherein the microorganism is selected from the group consisting of *Crypthecodinium cohnii* and the fungus *Mortierella alpina*.

17. The method of claim 1, where freezing is accomplished by a method selected from the group consisting of air freezing, blast freezing, fluidized-bed freezing, plate freezing, liquid immersion freezing, cryogenic freezing, liquid nitrogen freezing, dry ice freezing, and $CCl_2F_2$ freezing.

18. The method of claim 1, wherein comminuting is accomplished by the use of a comminution device selected from the group consisting of a crushing device, a grinding device, and a homogenization device.

19. The method of claim 1, wherein comminuting is accomplished by a pin mill.

20. The method of claim 1, wherein comminuting results in the comminuted biomass having a particle size range from about 8 μm to about 50 μm.

21. The method of claim 1, wherein extruding takes place at a temperature between about 10° C. and about 60° C.

22. The method of claim 1, wherein extruding takes place at a temperature of from about 20° C. and about 30° C.

23. The method of claim 1 wherein the dry agent is selected from the group consisting of plant starches, plant fibers, biomeal, oilseed hulls, rice flour and peanut hulls.

24. The method of claim 1 wherein the dry agent is added to the biomass at a final concentration of between about 1% by dry weight and about 50% by dry weight.

25. The method of claim 1 wherein the dry agent is added to the biomass at a final concentration of between about 5% by dry weight and about 30% by dry weight.

26. The method of claim 1 wherein the moisture content of the comminuted biomass prior to extrusion is less than about 25% by weight.

27. The method of claim 1, wherein the moisture content of the comminuted biomass prior to extrusion is about 10% by weight.

28. The method of claim 1, wherein about 50% of the volume of the comminuted biomass comprises air.

29. The method of claim 1, wherein the lipid is selected from the group consisting of acylglycerols, phosphoglycerides, fatty acids, sphingolipids, gangliosides, phospholipids, waxes, tocopherols, tocotrienols, triacylglycerols, sterols, carotenoids, pigments, polyphenols, and antioxidants.

30. The method of claim 1, wherein the lipid comprises a PUFA having a carbon chain length of at least 20.

31. The method of claim 1, wherein the lipid comprises a PUFA having a carbon chain length of at least 22.

32. The method of claim 1, wherein the lipid comprises a PUFA having at least three double bonds.

33. The method of claim 1, wherein the lipid comprises a PUFA comprising a lipid having at least four double bonds.

34. The method of claim 1, wherein the lipid comprises docosahexaenoic acid.

35. The method of claim 34, wherein the lipid comprises at least 55 weight percent docosahexaenoic acid.

36. The method of claim 1, wherein the lipid comprises docosapentaenoic acid.

37. The method of claim 1, wherein the lipid comprises arachidonic acid.

38. The method of claim 1, wherein the lipid comprises eicosapentaenoic acid.

39. The method of claim 1, wherein the percolation extraction is selected from the group consisting of aqueous solvent extraction, organic solvent extraction, near-critical solvent extraction, supercritical solvent extraction, enzyme-assisted extraction, microwave extraction and mechanical extraction.

40. The method of claim 1, wherein the percolation extraction is organic solvent extraction with a solvent selected from the group consisting of hexane and isohexane.

41. The method of claim 1, further comprising drying the extruded biomass prior to percolation extraction.

* * * * *